(12) United States Patent
Canham

(10) Patent No.: US 8,940,278 B2
(45) Date of Patent: Jan. 27, 2015

(54) ORAL HYGIENE COMPOSITIONS

(75) Inventor: Leigh Trevor Canham, Malvern (GB)

(73) Assignee: Intrinsiq Materials Global Limited, Dublin (IE)

(*) Notice: Subject to any disclaimer, the term of this patent is extended or adjusted under 35 U.S.C. 154(b) by 1595 days.

(21) Appl. No.: 11/918,572

(22) PCT Filed: Apr. 21, 2006

(86) PCT No.: PCT/GB2006/001459
§ 371 (c)(1),
(2), (4) Date: Jan. 23, 2009

(87) PCT Pub. No.: WO2006/111761
PCT Pub. Date: Oct. 26, 2006

(65) Prior Publication Data
US 2009/0214451 A1    Aug. 27, 2009

(30) Foreign Application Priority Data
Apr. 22, 2005    (GB) .................................. 0508174.0

(51) Int. Cl.
*A61K 8/18*    (2006.01)
*A61Q 11/00*   (2006.01)
*A61K 8/02*    (2006.01)
*A61K 8/25*    (2006.01)

(52) U.S. Cl.
CPC . *A61Q 11/00* (2013.01); *A61K 8/02* (2013.01); *A61K 8/25* (2013.01)
USPC ............................................ 424/49; 424/401

(58) Field of Classification Search
USPC ................................ 51/308; 428/450; 424/78
See application file for complete search history.

(56) References Cited

U.S. PATENT DOCUMENTS

| 4,421,527 A * | 12/1983 | Wason ............................. 51/308 |
| 4,440,745 A * | 4/1984  | Schmidt et al. ............. 424/78.03 |
| 5,279,815 A   | 1/1994  | Wason et al. |
| 6,322,895 B1* | 11/2001 | Canham ........................ 428/450 |
| 2002/0086039 A1* | 7/2002 | Lee et al. ....................... 424/401 |

FOREIGN PATENT DOCUMENTS

| EP | 1 637 171    | 3/2006 |
| JP | 61-289025 A  | 12/1986 |
| JP | 5-170630     | 7/1993 |
| JP | 6-279247     | 10/1994 |
| JP | 2001-064139 A | 3/2001 |
| JP | 2001-122611  | 5/2001 |
| WO | 97/06101     | 2/1997 |
| WO | 01/10392     | 2/2001 |
| WO | 02/15863     | 2/2002 |
| WO | 03/011251    | 2/2003 |

OTHER PUBLICATIONS

D.C. Smith, "Biomaterals in Dentistry". Journal of Dental Research 1975:54;B146-B152.*
PCT International Search Report mailed Jul. 6, 2006.
Written Opinion of the International Searching Authority mailed Jul. 6, 2006.
International Preliminary Report on Patentability dated Aug. 8, 2007.
Official Action and English translation in JP 2008-507166 mailed Dec. 20, 2011.

* cited by examiner

*Primary Examiner* — Walter Webb
(74) *Attorney, Agent, or Firm* — Nixon & Vanderhye P.C.

(57) ABSTRACT

Oral hygiene compositions suitable for use as dentifrice compositions comprising a silicon abrasive agent are provided.

33 Claims, 7 Drawing Sheets

ORAL HYGIENE COMPOSITIONS

This application is the U.S. national phase of International Application No. PCT/GB2006/001459 filed Apr. 21, 2006 which designated the U.S. and claims priority to GB 0508174.0 filed Apr. 22, 2005, the entire contents of each of which are hereby incorporated by reference.

FIELD OF THE INVENTION

This invention relates to oral hygiene compositions comprising silicon. The present invention also relates to methods of treatment using these compositions and methods for their production.

BACKGROUND OF THE INVENTION

Oral hygiene compositions suitable for use as dentifrice compositions such as toothpastes, and mouthwashes are well known. Modern dentifrices often contain an abrasive substance for the controlled mechanical cleaning and polishing of teeth, and optionally a number of other common ingredients, including humectants, binders, flavours, colours, therapeutic or active ingredients, such as a fluoride source, rheology control agents, preservatives, and foaming agents or detergents.

The primary function of the abrasive substance in such dentifrice formulations is to help remove various deposits, including pellicle film, from the surface of the teeth. Pellicle film adheres tightly to the teeth and often contains coloured constituents, which impart an unsightly appearance.

An effective dentifrice formulation should seek to maximise the removal of various deposits, including pellicle film. The abrasive used in such formulations is preferably selected so as not to damage gums, nor the hard tissues of teeth through abrasion or demineralisation of the hard teeth tissue. The abrasiveness of toothpastes results from abrasives such as silica, calcium phosphate, alumina or other solid particles in the toothpaste mechanically removing deposits and films from the teeth.

There is a continued need for alternative abrasives for use in dentifrice formulations such as toothpastes, which provide the necessary cleaning requirements, including pellicle film removal, and/or tartar inhibition combined with acceptable or improved levels of abrasiveness. Achieving this balance has hitherto proved challenging.

The present invention is based on the finding that silicon, and in particular porous silicon, may be used as an abrasive agent in oral hygiene compositions including those suitable for use as dentifrice compositions.

SUMMARY OF THE INVENTION

In a first aspect of the present invention, an oral hygiene composition, for example a dentifrice composition, comprising a particulate silicon abrasive agent is provided.

Optionally the silicon abrasive agent may be loaded with one or more active and/or inactive agents for controlled release to the teeth and/or other oral surfaces.

According to a further aspect of the present invention, there is provided a production process for said oral hygiene composition according to the first aspect of the present invention, comprising blending said particulate silicon abrasive agent and other components of the oral hygiene composition.

According to a further aspect of the present invention, a method for reducing stain and/or plaque and/or gingivitis comprising the application of a safe and effective amount of a composition according to the first aspect of the invention to the teeth and other oral surfaces is provided.

According to a further aspect of the present invention, the use of a composition according to the first aspect of the invention in the manufacture of a medicinal oral hygiene composition, such as a dentifrice composition, for reducing plaque and/or for reducing or inhibiting gingivitis is provided.

According to a further aspect of the present invention, a cosmetic method for reducing stain comprising the application of a safe and effective amount of a composition according to the first aspect of the invention to the teeth and other oral surfaces is provided.

According to a further aspect of the present invention, a composition according to the first aspect of the invention for use in the treatment and/or the prevention of plaque and/or gingivitis is provided.

DETAILED DESCRIPTION OF THE INVENTION

Silicon

As used herein, and unless otherwise stated, the term "silicon" refers to elemental silicon. Elemental silicon is usually described as being dark grey in colour. For the avoidance of doubt, and unless otherwise stated, it does not include silicon-containing chemical compounds such as silica, silicates or silicones, although it may be used in combination with these materials.

In particular, the silicon abrasive agent which is suitable for use in the present invention may be chosen from amorphous silicon, single crystal silicon and polycrystalline silicon (including nanocrystalline silicon, the grain size of which is typically taken to be 1 to 100 nm) and including combinations thereof. Porous silicon, which may be referred to as "pSi" is preferred and any of the above-mentioned types of silicon, which are suitable for use in the present invention, may be porosified. The silicon may be surface porosified, for example, using a stain etch method or more substantially porosified, for example, using an anodisation technique.

Most preferably, the silicon is resorbable. The silicon may be present as an abrasive agent and/or for the controlled delivery of active and/or inactive agents. The silicon abrasive agent may comprise bioactive silicon.

The silicon abrasive agent may be about 95 to 99.99999% pure, for example about 96 to 99.9% pure. So-called metallurgical grade silicon is preferred which typically has a purity of about 98 to 99.5%.

The use of the semiconductor, silicon, in biological applications is described, for example, in PCT/GB96/01863, the contents of which are hereby incorporated by reference in their entirety. As described therein, bulk crystalline silicon can be rendered porous by partial electrochemical dissolution in hydrofluoric acid based solutions, as described in U.S. Pat. No. 5,348,618, the contents of which are also hereby incorporated by reference in their entirety. This etching process generates a silicon structure that retains the crystallinity and the crystallographic orientation of the original bulk material. Hence, the porous silicon formed is a form of crystalline silicon. Broadly, the method involves anodising, for example, a heavily boron doped CZ silicon wafer in an electrochemical cell which contains an electrolyte comprising a 10% solution of hydrofluoric acid in ethanol. Following the passing of an anodisation current with a density of about 50 mA cm$^{-2}$, a porous silicon layer is produced which may be separated from the wafer by increasing the current density for a short period of time. The effect of this is to dissolve the silicon at the interface between the porous and bulk crystalline regions.

PCT/GB02/03493 and references therein, the contents of which are hereby incorporated by reference in their entirety, also describes methods for making particles of silicon, said methods being suitable for making silicon for use in the present invention.

Following its formation, the porous silicon may be dried. For example, it may be supercritically dried as described by Canham in Nature, vol. 368, pp133-135, (1994). Alternatively, the porous silicon may be freeze dried or air dried using liquids of lower surface tension than water, such as ethanol or pentane, as described by Bellet and Canham in Adv. Mater, 10, pp487490, (1998).

To produce silicon in a particulate form suitable for use in the oral hygiene composition, the silicon may be subjected to comminution. For example, the particle size may be reduced by milling as described in Kerkar et al. J. Am. Ceram. Soc., vol. 73, pp 2879-2885, (1990). Other methods for producing particulate silicon are described in PCT/GB01/03633, the contents of which are hereby incorporated by reference in their entirety, in which the silicon is subjected to centrifuge methods, or silicon particles may be produced by grinding silicon powders. Porous silicon powders may be ground between wafers of crystalline silicon. Since porous silicon has lower hardness than bulk crystalline silicon, and crystalline silicon wafers have ultrapure, ultrasmooth surfaces, a silicon wafer/porous silicon powder/silicon wafer sandwich is a convenient means of achieving for instance, a 1-10 µm particle size from much larger porous silicon particles derived, for example, via anodisation.

The mean particle size ($d_{50}$/µm) of the silicon particles is measured using a Malvern Particle Size Analyzer, Model Mastersizer, from Malvern Instruments. A helium-neon gas laser beam is projected through a transparent cell which contains the silicon particles suspended in an aqueous solution. Light rays which strike the particles are scattered through angles which are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the silicon.

The mean particle size of the particulate silicon abrasive agent is preferably such that the balance of abrasive and cleaning characteristics of the dentifrice composition are as effective as reasonably possible without causing damage to the teeth and/or gums. Typically $d_{50}$ lies in the range 1 to 100 µm and preferably in the range 10 to 50 µm. For example, $d_{50}$ is about 30 µm.

When the silicon abrasive agent comprises porous silicon, the surface of the porous silicon may be suitably modified in order, for example, to improve the stability of the porous silicon in the oral hygiene composition. In particular, the surface of the porous silicon may be modified to render the silicon more stable in alkaline conditions. The surface of the porous silicon may include the external and/or internal surfaces formed by the pores of the porous silicon. The surfaces of the porous silicon may therefore be modified to provide: silicon hydride surfaces; silicon oxide surfaces wherein the porous silicon may typically be described as being partially oxidised; or derivatised surfaces which may possess Si—O—C bonds and/or Si—C bonds.

Silicon hydride surfaces may, for example, be generated by stain etch or anodisation methods using hydrofluoric acid based solutions. Silicon oxide surfaces may be produced by subjecting the silicon particles to chemical oxidation, photo-chemical oxidation or thermal oxidation, as described for example in Chapter 5.3 of Properties of Porous Silicon (edited by L. T. Canham, IEE 1997). PCT/GB02/03731, the entire contents of which are hereby incorporated by reference, describes how porous silicon may be partially oxidised in such a manner that the sample of porous silicon retains some porous silicon in an unoxidised state. For example, PCT/GB02/03731 describes how, following anodisation in 20% ethanoic HF, the anodised sample was partially oxidised by thermal treatment in air at 500° C. to yield a partially oxidised porous silicon sample.

Following partial oxidation, the silicon particles may be partially oxidised to possess an oxide content corresponding to between about one monolayer of oxygen and a total oxide thickness of less than or equal to about 4.5 nm covering the entire silicon skeleton. The porous silicon may have an oxygen to silicon atomic ratio between about 0.04 and 2.0, and preferably between 0.60 and 1.5. Oxidation may occur in the pores and/or on the external surface of the silicon.

Derivatised porous silicon is porous silicon possessing a covalently bound monolayer on at least part of its surface. The monolayer typically comprises one or more organic groups that are bonded by hydrosilylation to at least part of the surface of the porous silicon. Derivatised porous silicon is described in PCT/GB00/01450, the contents of which are hereby incorporated by reference in their entirety. PCT/GB00/01450 describes derivatisation of the surface of silicon using methods such as hydrosilyation in the presence of a Lewis acid. In that case, the derivatisation is effected in order to block oxidation of the silicon atoms at the surface and so stabilise the silicon. Methods of preparing derivatised porous silicon are known to the skilled person and are described, for example, by J. H. Song and M. J. Sailor in Inorg. Chem., vol 21, No. 1-3, pp 69-84, 1999 (Chemical Modification of Crystalline Porous Silicon Surfaces). Derivitisation of the silicon may be desirable when it is required to increase the hydrophobicity of the silicon, thereby decreasing its wettability. Preferred derivatised surfaces are modified with one or more alkyne groups. Alkyne derivatised silicon may be derived from treatment with acetylene gas, for example, as described in "Studies of thermally carbonized porous silicon surfaces" by J. Salonen et al in Phys Stat. Solidi (a), 182, pp123-126, (2000) and "Stabilisation of porous silicon surface by low temperature photoassisted reaction with acetylene", by S. T. Lakshmikumar et al in Curr. Appl. Phys. 3, pp185-189 (2003).

Porous silicon may be subdivided according to the nature of its porosity. Microporous silicon contains pores having a diameter less than 2 nm; mesoporous silicon contains pores having a diameter in the range 2 to 50 nm; and macroporous silicon contains pores having a diameter greater than 50 nm. The silicon abrasive agent according to the present invention may comprise porous silicon which is microporous or mesoporous.

One convenient way of achieving the desired hardness for the silicon abrasive agent, is to control the porosity of the silicon. Methods for controlling the porosity of porous silicon are well known. Both microporous and mesoporous silicon may be used in the oral hygiene compositions of the present invention. The choice of which porous silicon to use may, to some extent, depend on whether or not it is desired to use the porous silicon as a vehicle for the controlled release of an active or inactive agent. Typically, the porous silicon abrasive agent according to the present invention may possess a BET surface area in the range of 100 to 700 $m^2$/g, for example 200 to 500 $m^2$/g. The BET surface area is determined by a BET nitrogen adsorption method as described in Brunauer et al., J.

Am. Chem. Soc., 60, 309, 1938. The BET measurement is performed using an Accelerated Surface Area and Porosimetry Analyser (ASAP 2400) available from Micromeritics Instrument Corporation, Norcross, Ga. 30093. The sample is outgassed under vacuum at 350° C. for a minimum of 2 hours before measurement. Generally, the degree of porosity is at least about 30 vol %, for example at least about 40 vol %, for example at least about 50 vol %, for example at least about 70 vol %, for example at least about 75 vol %, for example about 80 vol % and up to about 85 vol % or 90 vol %. For use primarily as an abrasive, the degree of porosity is typically about 30 to 70 vol %, preferably about 50 to 70 vol %. It is also possible to blend proportions of porous silicon which possess different ranges of porosity. For example, in order to provide a composition which, in addition to providing acceptable abrasive characteristics, also controls the rate at which the flavour is released then a proportion of the porous silicon particles may possess a significantly different porosity. For example, in the event an initial burst of flavour is required, then a significant proportion of the silicon particles may advantageously possess a porosity of at least about 75 vol %, for example at least about 80 vol % and up to about 85 vol % or 90 vol %. Typically the proportion of the higher porosity silicon will lie in the range of about 5 to 60 vol %.

The Mohs hardness of the silicon for use in the present invention is typically equal to or greater than about 2 and may be less than or equal to about 5. Preferably the Mohs hardness is 3 to 4. The test corresponding to the Mohs hardness scale is a well known one where hardness is defined as that material's ability to inflict scratches on another material. The scale is from 1 to 10 with the higher number indicating increasing hardness.

Another well known method for measuring hardness is the Vickers hardness test. This test is a measure of the hardness of a material calculated from the size of an impression produced under load by a pyramid-shaped diamond indenter. The indenter employed in the Vickers test is a square-based pyramid whose opposite sides meet at the apex at an angle of 136°. The diamond is pressed into the surface of the material at loads ranging up to approximately 120 kg-force, and the size of the impression (usually no more than 0.5 mm) is measured with the aid of a calibrated microscope such as a filar microscope. The Vickers number (HV) is calculated using the following formula:

$$HV = 1.854(F/D2)$$

wherein F is the applied load (kg-force) and D2 is the area of the indentation (mm$^2$). The Vickers hardness of the silicon for use in the present invention is, for example, typically greater than 1 GPa, for example 1 to 4 GPa. Preferably, the Vickers hardness is less than 4 GPa or 3 GPa, for example 1 to 2 GPa.

Some forms of silicon, in particular mesoporous silicon, are resorbable. Resorbable silicon is silicon which dissolves over a period of time when immersed in simulated body fluid solution such as intestinal fluid. The by-product of resorbable silicon in the body is silicic acid. The silicon abrasive for use in the oral hygiene formulations according to the present invention may be resorbable and may be loaded with one or more active and/or non-active agents for delivery to the teeth and other oral surfaces. For example, any one or more of antitartar agents, flavouring agents, antiseptics or fluoride may be released in a controlled manner using this method. The delivery of antiseptics such as chlorhexidine is particularly preferred. The porous silicon may be engineered to control the kinetics of the release of the active and/or non-active agents. This controlled release may be achieved by controlling one or more of the pore size, the level of porosity and the size of the silicon particles.

The agents to be delivered may be loaded onto the silicon in various ways. For example, the one or more agents may be deposited onto the surface of the silicon particles, incorporated into the pores of porous silicon or bound or otherwise associated with the surface of the silicon.

The agent to be delivered may be dissolved or suspended in a suitable solvent, and silicon particles may be incubated in the resulting solution for a suitable period of time. Removal of solvent will result in the agent being deposited on the surface of the silicon particles. However, if the particles comprise porous silicon, the solution of the active or inactive agent will penetrate into the pores of the porous silicon by capillary action, and, following solvent removal, the agent will be present in the pores.

The agent to be delivered may be loaded onto the silicon either before and/or after the comminution (e.g. grinding), process.

The total quantity of abrasive present in the oral hygiene compositions, more particularly the dentifrice composition according to the present invention, is about 5 to 50 wt %, preferably from about 20 to 40 wt %. When the dentifrice composition is a toothpowder then the amount of abrasive may be higher and as much as 95 wt %. The abrasive may comprise abrasives other than the abrasive silicon agent according to the present invention or the abrasive silicon agent may constitute all or substantially all of the abrasive in the dentifrice composition.

The use of silicon in the oral hygiene compositions according to the present invention may also impart a visually appealing appearance to the oral hygiene composition, which may include a glittering or glinting appearance. For example, PCT/GB01/03633, the contents of which are hereby incorporated by reference in their entirety, describes the use of mirrors comprising layers, which in turn comprise one or more of crystalline silicon, porous silicon, amorphous silicon and polycrystalline silicon in dermatological compositions. By using mirrors, which reflect different wavelengths of light, specific colouration of compositions may be effected. This may be achieved by varying the porosities of adjacent layers comprising porous silicon between low and high porosity layers. Typically, the low porosity layers may have a porosity of up to about 65 vol %, for example about 25 vol % to 65 vol % and the high porosity layers have a porosity of at least about 60 vol %, for example about 60 vol % to 95 vol %. Each layer may comprise greater than 10 layers or greater than 100 layers, or greater than 200 layers or greater than or equal to 400 layers. Each layer from which the mirrors are formed has a different refractive index to its neighbouring layer or layers such that the combined layers form a Bragg stack mirror. In particular, the glittering or glinting appearance may be applied to gels, typically those which are translucent in nature.

Bioactivity

Bioactive materials are highly compatible with living tissue and capable of forming a bond with tissue by eliciting a specific biological response. Bioactive materials may also be referred to as surface reactive biomaterials. Bioactive silicon comprises a nanostructure and such nanostructures include: (i) microporous silicon, mesoporous silicon either of which may be single crystal silicon, polycrystalline silicon or amorphous silicon; (ii) polycrystalline silicon with nanometer size grains; (iii) nanoparticles of silicon which may be amorphous or crystalline. Preferably, for use as a bioactive material, the silicon abrasive agent is microporous.

Though not wishing to be bound by a particular theory, it is believed that the use of bioactive silicon, according to the present invention, generates silicic acid in-situ which promotes remineralisation of the tooth. The bioactive silicon may comprise additional components such as a source of calcium and/or phosphate and/or fluoride in order to aid, for example, in the remineralisation process. This includes the remineralisation of subsurface dental enamel and/or mineralising tubules in dentin thereby counteracting caries and/or hypersensitivity. Suitable calcium, phosphate and fluoride compounds are well known in the art. At least about 10 ppm of calcium ions may be present, with the upper limit being about 35,000 ppm. The concentration of phosphate ions may typically be in the range of about 250 to 40,000 ppm.

Dentifrice Composition "Dentifrice composition" as used herein, includes a toothpaste, tooth powder, prophylaxis paste, lozenge, dragee, bon-bon, gum or oral gel. The oral gel may be of the type suitable for use in multi-stage whitening systems. The dentifrice composition, in which the particulate silicon abrasive is used according to the present invention, will comprise constituents well known to one of ordinary skill; these may broadly be characterised as active and inactive agents. Active agents include anticaries agents such as fluoride, antibacterial agents, desensitising agents, antitartar agents (or anticalculus agents) and whitening agents. Inactive ingredients are generally taken to include water (to enable the formation of a water phase), detergents, surfactants or foaming agents, thickening or gelling agents, binding agents, efficacy enhancing agents, humectants to retain moisture, flavouring, sweetening and colouring agents, preservatives and, optionally in addition to the silicon abrasive of the present invention, further abrasives for cleaning and polishing.

Waterphase

The dentifrice composition typically comprises a waterphase which comprises an humectant. Water may be present in an amount of from about 1 to about 90 wt %, preferably from about 10 to about 60 wt %. Preferably, the water is deionised and free of organic impurities.

Any of the known humectants for use in dentifrice compositions may be used. Suitable examples include sorbitol, glycerin, xylitol, propylene glycol. The humectant is typically present in an amount of about 5 to 85 wt % of the dentifrice composition.

Anticaries Agent

The dentifrice composition according to the present invention may comprise an anticaries agent, such as a source of fluoride ions. The source of fluoride ions should be sufficient to supply about 25 ppm to 5000 ppm of fluoride ions, for example about 525 to 1450 ppm. Suitable examples of anticaries agents include one or more inorganic salts such as soluble alkali metal salts including sodium fluoride, potassium fluoride, ammonium fluorosilicate, sodium fluorosilicate, sodium monofluorophosphate, and tin fluorides such as stannous fluoride.

Antitartar Agents

Any of the known antitartar agents may be used in the dentifrice compositions according to the present invention. Suitable examples of antitartar agents include pyrophosphate salts, such as dialkali or tetraalkali metal pyrophosphate salts, long chain polyphosphates such as sodium hexametaphosphate and cyclic phosphates such as sodium trimetaphosphate. These antitartar agents are included in the dentifrice composition at a concentration of about 1 to about 5 wt %.

Antibacterial Agents

Any of the known antibacterial agents may be used in the compositions of the present invention. For example, these include non-cationic antibacterial agents such as halogenated diphenyl ethers, a preferred example being triclosan (2,4,4'-trichloro-2'-hydroxydiphenyl ether). The antibacterial agent(s) may be present in an amount of about 0.1 to 1.0 wt % of the dentifrice composition, for example about 0.3 wt %.

Other Abrasive Agents

The particulate silicon can be used as the sole abrasive in preparing the dentifrice composition according to the present invention or in combination with other known dentifrice abrasives or polishing agents. Commercially available abrasives may be used in combination with the silicon and include silica, aluminium silicate, calcined alumina, sodium metaphosphate, potassium metaphosphate, calcium carbonate, calcium phosphates such as tricalcium phosphate and dehydrated dicalcium phosphate, aluminium silicate, bentonite or other siliceous materials, or combinations thereof.

Flavours

The dentifrice composition of the present invention may also contain a flavouring agent. Suitable examples include essential oils such as spearmint, peppermint, wintergreen, sassafras, clove, sage, eucalyptus, majoram, cinnamon, lemon, lime, grapefruit, and orange. Other examples include flavouring aldehydes, esters and alcohols. Further examples include menthol, carvone, and anethole.

Thickening Agents

The thickening agent may be present in the dentifrice composition in amounts of about 0.1 to about 10% by weight, preferably about 0.5 to about 4% by weight.

Thickeners used in the compositions of the present invention include natural and synthetic gums and colloids, examples of which include xanthan gum, carrageenan, sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Suitable thickeners also include inorganic thickeners such as amorphous silica compounds including colloidal silica compounds.

Surfactants

Surfactants may be used in the compositions of the present invention to achieve increased prophylactic action and render the dentifrice compositions more cosmetically acceptable. The surfactant is typically present in the dentifrice compositions according to the present invention in an amount of about 0.1 to about 5 wt %, preferably about 0.5 to about 2 wt %. The dentifrice compositions according to the present invention may comprise one or more surfactants, which may be selected from anionic, non-ionic, amphoteric and zwitterionic surfactants. The surfactant is preferably a detersive material, which imparts to the composition detersive and foaming properties. Suitable examples of surfactants are well known to an ordinary skilled person and include water-soluble salts of higher fatty acid monoglyceride monosulfates, such as the sodium salt of the monosulfated monoglyceride of hydgrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals. Further examples include N-lauroyl sarcosine, and the sodium, potassium, and ethanolamine salts of N-lauroyl, N-myristoyl, or N-palmitoyl sarcosine.

Efficacy Enhancing Agents

One or more efficacy enhancing agents for any antibacterial, antitartar or other active agent within the dentifrice composition may also be included in the dentifrice composition. Suitable examples of efficacy enhancing agents include synthetic anionic polycarboxylates. Such anionic polycarboxylates may be employed in the form of their free acids or partially, or more preferably, fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000.

When present, the efficacy enhancing agent, for example the anionic polycarboxylate, is used in amounts effective to achieve the desired enhancement of the efficacy of any antibacterial, antitartar or other active agent within the dentifrice composition. Generally, the anionic polycarboxylate(s) are present within the dentifrice composition from about 0.05 wt % to about 4 wt %, preferably from about 0.5 wt % to about 2.5 wt %.

Other Ingredients

Various other materials may be incorporated in the dentifrice compositions of this invention, including: preservatives; silicones; desensitizers, such as potassium nitrate; whitening agents, such as hydrogen peroxide, calcium peroxide and urea peroxide; and chlorophyll compounds. Some toothpastes include bicarbonate in order to reduce the acidity of dental plaque. These additives, when present, are incorporated in the dentifrice composition in amounts which do not substantially adversely affect the desired properties and characteristics.

Preparation of the Dentifrice Composition

Suitable methods for making the dentifrice compositions according to the present invention include the use of high shear mixing systems under vacuum. In general, the preparation of dentifrices is well known in the art. U.S. Pat. No. 3,980,767, U.S. Pat. No. 3,996,863, U.S. Pat. No. 4,358,437, and U.S. Pat. No. 4,328,205, the contents of which are hereby incorporated by reference in their entirety, describe suitable methods for making dentifrice compositions.

For example, in order to prepare a typical dentifrice composition according to the present invention, an humectant may be dispersed in water in a conventional mixer under agitation. Organic thickeners are combined with the dispersion of humectant along with: any efficacy enhancing agents; any salts, including anticaries agents such as sodium fluoride; and any sweeteners. The resultant mixture is agitated until a homogeneous gel phase is formed. One or more pigments such as titanium dioxide may be combined with the gel phase along with any acid or base required to adjust the pH. These ingredients are mixed until an homogenous phase is obtained. The mixture is then transferred to a high speed/vacuum mixer, wherein further thickener and surfactant ingredients may be combined with the mixture. Any abrasives, including the silicon abrasive, may be combined with the mixture, along with other abrasives to be used in the composition. Any water insoluble antibacterial agents, such as triclosan, may be solubilized in the flavour oils to be included in the dentifrice composition and the resulting solution is combined along with the surfactants with the mixture, which is then mixed at high speed for about 5 to 30 minutes, under vacuum of from about 20 to 50 mm of Hg. The resultant product is typically an homogeneous, semi-solid, extrudable paste or gel product.

The pH of the dentifrice composition is typically such that the silicon will not dissolve in the composition over a significant period of time and will thus afford an acceptable shelf-life. The pH of the dentifrice composition is typically less than or equal to about 9 and preferably, particularly for compositions other than powders such as toothpastes, less than or equal to about 7. The lower limit of pH may typically be about 3.5 or about 4. In particular, the pH may be about 3.5 or about 4 when the dentifrice composition is a gel, such as those used in multi-stage whitening systems.

The abrasivity of the dentifrice compositions of the present invention, containing the silicon abrasive agent, can be determined by means of Radioactive Dentine Abrasion (RDA) values as determined according to the method recommended by the American Dental Association, as described by Hefferren, J. Dental Research, vol. 55 (4), pp 563-573, (1976) and described in U.S. Pat. No. 4,340,583, U.S. Pat. No. 4,420,312 and U.S. Pat. No. 4,421,527, the contents of which are contained herein by reference in their entirety. In this procedure, extracted human teeth are irradiated with a neutron flux and subjected to a standard brushing regime. The radioactive phosphorus 32 removed from the dentin in the roots is used as the index of the abrasion of the dentifrice tested. A reference slurry containing 10 g of calcium pyrophosphate in 15 ml of a 0.5% aqueous solution of sodium carboxymethyl cellulose is also measured and the RDA of this mixture is arbitrarily taken as 100. The dentifrice composition to be tested is prepared as a suspension at the same concentration as the pyrophosphate and submitted to the same brushing regime. The RDA of the dentifrice compositions according to the present invention may lie in the range of about 10 to 150, preferably less than about 100 and most preferably less than about 70.

The pellicle cleaning ratio (PCR) of the dentifrice compositions of the present invention is a measurement of the cleaning characteristics of dentifrices and generally may range from about 20 to 150 and is preferably greater than about 50.

The PCR cleaning values can be determined by a test described by Stookey et al., J. Dental Research, vol. 61 (11), pp 1236-9, (1982). Cleaning is assessed in vitro by staining 10 $mm^2$ bovine enamel specimens embedded in resin, which are acid etched to expedite stain accumulation and adherence. The staining is achieved with a broth prepared from tea, coffee and finely ground gastric mucin dissolved into a sterilized trypticase soy broth containing a 24-hour Sarcina lutea turtox culture. After staining, the specimens are mounted on a V-8 cross-brushing machine equipped with soft nylon toothbrushes adjusted to 150 g tension on the enamel surface. The specimens are then brushed with the dentifrice composition to be tested and a calcium pyrophosphate standard which comprises 10 g of calcium pyrophosphate in 50 ml of 0.5% aqueous solution of sodium carboxymethyl cellulose. The specimens are brushed with dentifrice slurries consisting of 25 g of toothpaste in 40 g of deionized water, for 400 strokes. The specimens are cleaned with Pennwalt pumice flour until the stain is removed. Reflectance measurements are taken using a Minolta Colorimeter using the standard Commission Internationale de l'Eclairage (CIE) L*a*b* scale in order to measure the colour of the specimens before and after brushing.

The cleaning efficiency of the dentifrice compositions according to the present invention, which is a measure of the ratio of PCR/RDA, may lie in the range from about 0.5 to about 2.0, is preferably greater than about 1.0 and more preferably greater than about 1.5.

BRIEF DESCRIPTION OF THE DRAWINGS

Embodiments of the invention will now be described, by way of example only and without limitation, with reference to the accompanying drawings, in which.

EXAMPLES

Embodiments of the present invention will now be described by way of example only, with reference to the following examples.

Example 1

Chemical Stability in Dentifrice Compositions

A bulk silicon wafer, coated with a layer of mesoporous silicon (650 nm thickness, 70 vol % porosity) was diced into segments which were half immersed into toothpastes having a pH of 6.1, 6.7 and 9.1 for a period of two days at 18° C. The results indicated that the mesoporous silicon was most stable in the toothpaste possessing a pH of 6.1 and least stable in the toothpaste possessing a pH of 9.1. At pH 6.1, little or no oxidation and/or corrosion of the mesoporous silicon had taken place.

Example 2

Chemical Stability in Human Saliva

Human saliva was collected in the morning from ten healthy adult volunteers between the ages of 20 and 50. Each volunteer rinsed their mouth with tap water, swallowed, waited for approximately 30 seconds and then spat into a collecting vessel. The pooled liquid had a pH of 7.5+/−0.1 at 26° C. Wafer segments containing a mesoporous (about 69 vol %) silicon layer of 0.63 µm+/−0.021 µm thickness were then incubated in 2 ml aliquots of saliva at 37° C. for periods ranging from 20 minutes to 5 hours. Cross sectional SEM images were taken of the mesoporous layer following exposure to the saliva in order to determine the change in thickness of the segments. After 20 minutes, the thickness had reduced to 0.61 µm; after 2 hours the thickness had reduced to 0.59 µm; and after 5 hours the thickness had reduced to 0.58 µm.

Example 3

Adhesion to Oral Surfaces

Figure 1A:
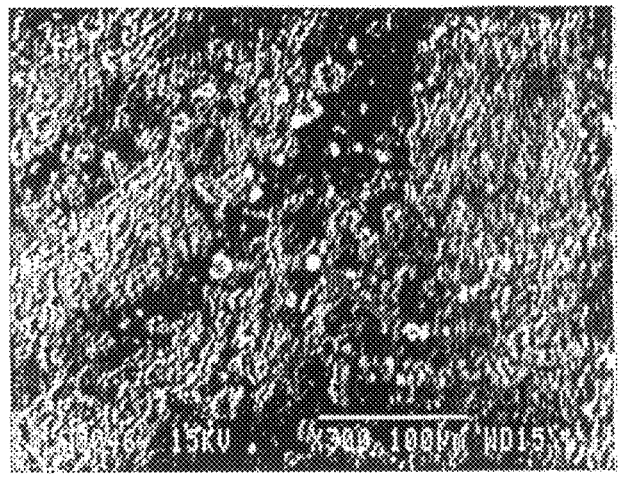
FIG. 1a is an SEM image (300×) of the roughened crown region of a human pre-molar tooth after brushing with unmodified commercially available toothpaste.
Figure 1B:
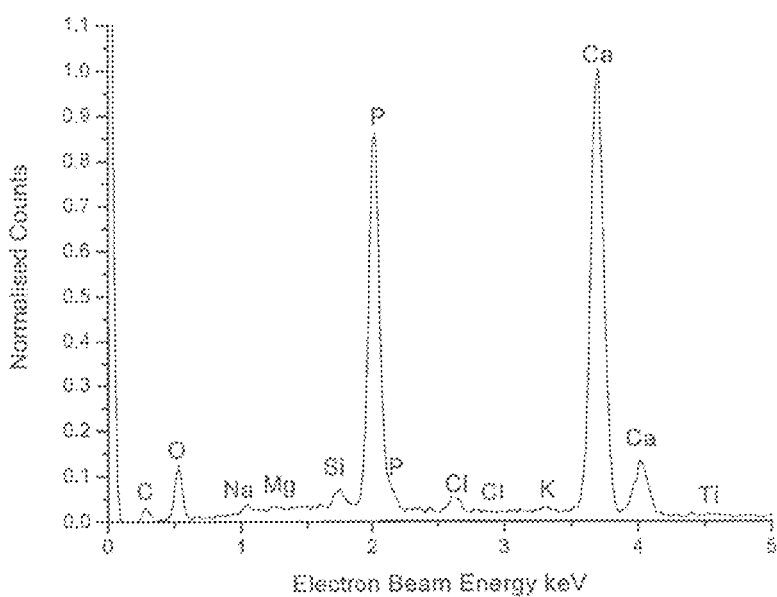
FIG. 1*b* is an EDX spectrum (15 keV beam, magnification 300) of the area shown in FIG. 1*a*.
Figure 1C:
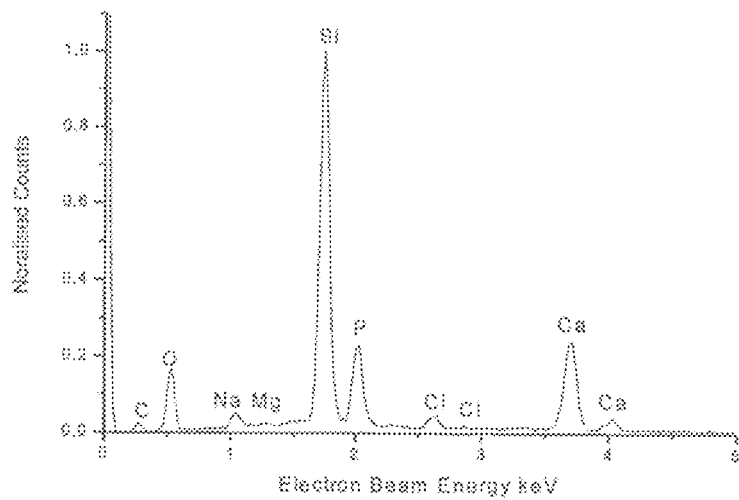
FIG. 1*c* is an EDX spectrum (15 keV beam, magnification 37000) focussing on one of the rounded particles in FIG. 1*a*.
Figure 2:
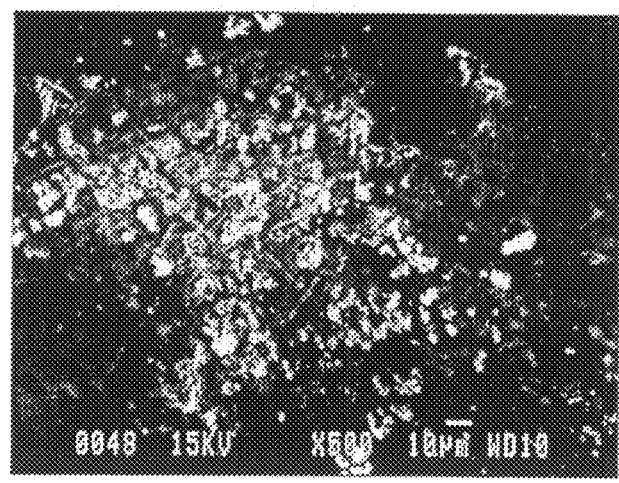
FIG. 2 is an SEM image (500×) of a highly porous region of the same crown shown in FIG. 1*a*.
Figure 3A:
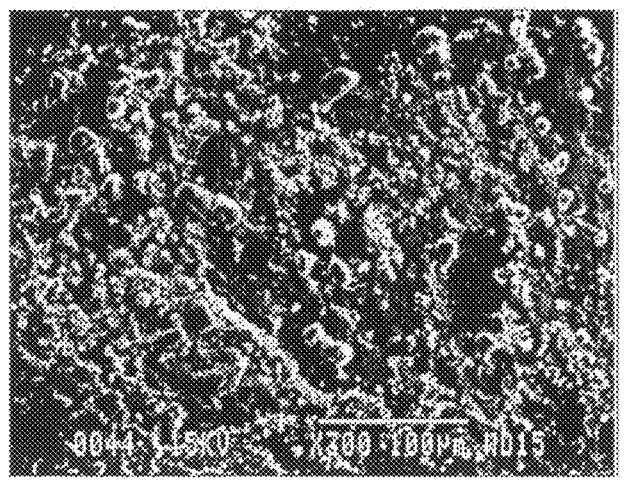
FIG. 3*a* is an SEM image (300×) of the roughened region of a human tooth, after brushing with a toothpaste according to the present invention.
Figure 3B:
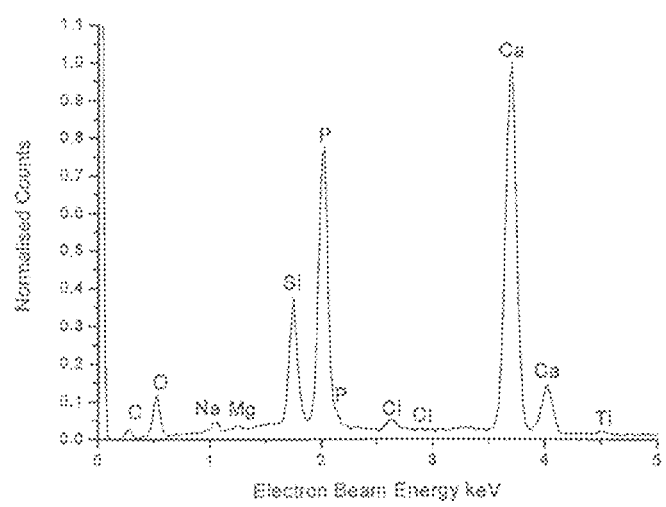
FIG. 3*b* is an EDX spectrum (15 keV beam, magnification 300) of the area shown in FIG. 3*a*.
Figure 3C:
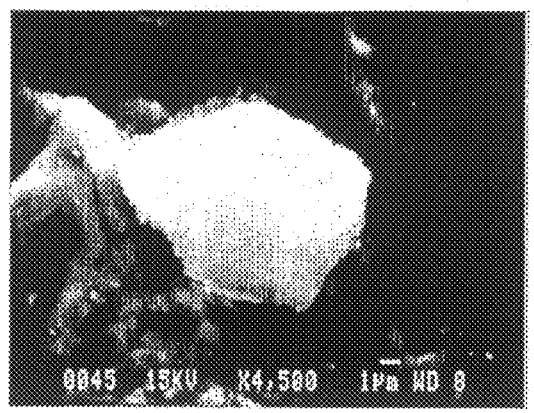
FIG. 3*c* is an SEM image (4,500×) of an angular particle shown in FIG. 3*a*.
Figure 3D:
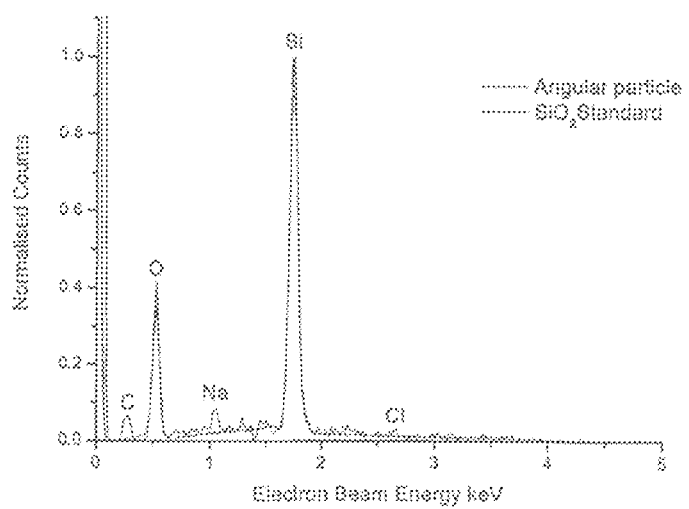
FIG. 3*d* is an EDX spectrum (5 keV beam, magnification 23000) of the particle shown in FIG. 3*c* compared to a non porous silica standard.

Extracted human pre-molars of 20-24 mm length were subjected to a 1 minute brush with Colgate® Total toothpaste (pH 6.7 prior to use), with and without 10 wt % mesoporous silicon glitter particles. These were prepared from fully porous silicon membranes. The membranes were fabricated by anodising 5-15 milliohm silicon wafers in methanol/40 wt % HF (1:1 by volume) electrolyte. The current density was modulated under computer control between 20 mA/cm$^{-2}$ (9 second periods) and 125 mA/cm$^{-2}$ (4.5 second periods) with 1 second periods in between where no current was applied. One hundred repeats generated vividly coloured layered structures with modulated porosity. Detachment of the membrane from the underlying non porous wafer was achieved by applying a final current pulse of 165 mA/cm$^{-2}$ for 30 seconds. The air dried membranes were then mechanically crushed into glitter powder by using a pestle and mortar, and were used without subsequent classification or sieving. Manual brushing was followed by a 5 minute water rinse of the surface of the tooth. FIG. 1*a* shows a 300× image of a roughened region of the crown surface after brushing with un-modified toothpaste. There is a low density of round hydrated silica particles present on the enamel surface. The associated EDX spectrum (15 keV beam, magnification 300) in FIG. 1*b*, shows a weak Si peak and dominant calcium phosphate peaks, which are characteristic of hydroxyapatite. FIG. 1*c* shows the EDX spectrum (15 keV beam, magnification 37000) focussing on one of the rounded particles in FIG. 1*a*. A highly porous region of the same crown is shown in FIG. 2 where there is shown a higher density of silica particles which are partially embedded in the enamel pores following brushing. FIG. 3*a* shows a 300× image of a roughened region of a different tooth, subjected to similar brushing but this time with the modified toothpaste. Following rinsing, both rounded and angular particles were still evident on the enamel surface following water rinsing. The associated EDX spectrum (15 keV beam, magnification 300) shown in FIG. 3*b* indicates that a significantly higher level of silicon is present, when compared to FIG. 1*a*. FIG. 3*c* shows a 4,500× image of an angular particle from FIG. 3*a*. Its angular shape is consistent with it being fractured porous silicon. The associated EDX spectrum (5 keV beam, magnification 23000) in FIG. 3*d* indicates that the porous silicon particle is heavily oxidised and/or hydrated. The "angular particle" spectrum in FIG. 3*d* shows dominant peaks due to the presence of Si and O and minor peaks (not evident in the "SiO$_2$ standard" spectrum) due to the presence of C, Na and Cl.

Example 4

Adhesion to Oral Surfaces (Surface Chemistry)

Figure 4A:
FIG. 4*a* is an SEM image (1000×) of the porosified part of the enamel of a human tooth exposed to untreated bulk silicon powder solution.
Figure 4B:
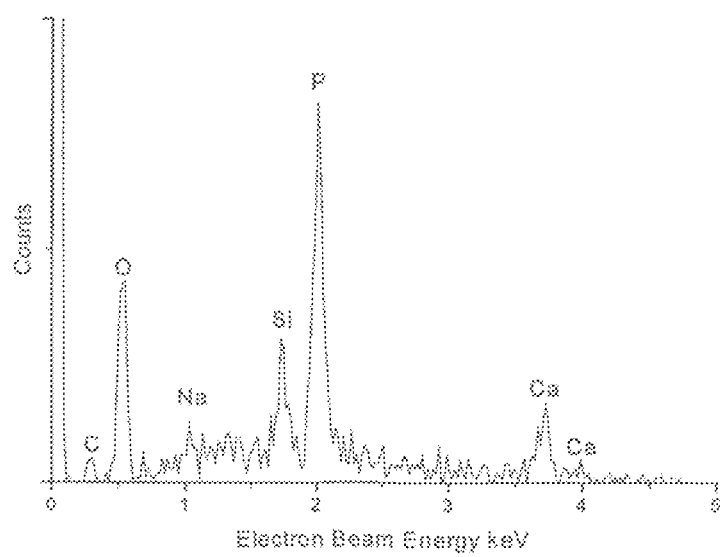
FIG. 4*b* is an EDX spectrum (5 keV beam, magnification 17000) of the area shown in FIG. 4*a*.
Figure 4C:
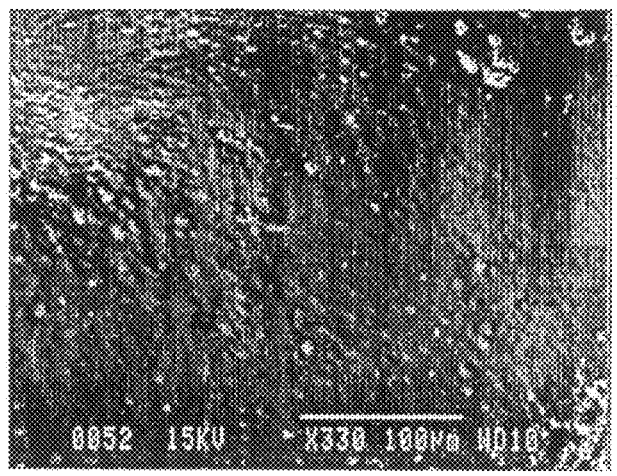
FIG. 4*c* is an SEM image (330×) of a relatively smooth region of a human tooth exposed to bulk silicon powder, in solution, which has been HF treated.
Figure 4D:
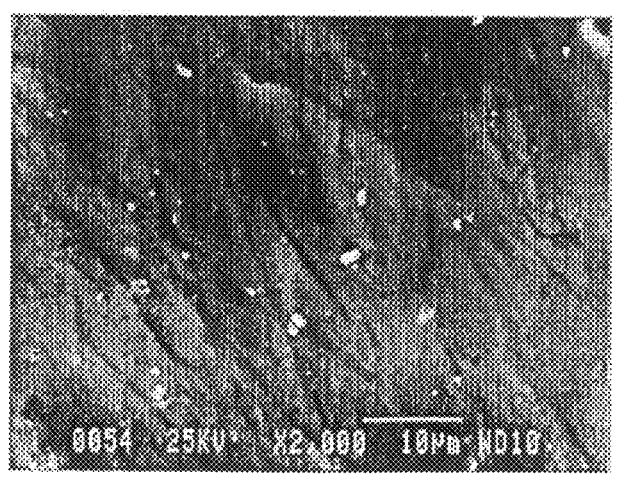
FIG. 4*d* is the SEM image in FIG. 4*c* but magnified 2000×.

Non-porous bulk metallurgical grade silicon particles, with and without native oxide surfaces were tested for their ability to adhere to oral surfaces. The particle size distribution was measured using a Malvern Instruments Mastersizer 2000, in conjunction with a Hydro G dispersion unit and the application of Mie scattering theory with version 5.22 software. The volume weighted mean particle diameter was 24 µm with a $d_{10}$ of 2.6 µm (i.e. 10% of particles by volume possess a diameter less than 2.6 µm) and a $d_{90}$ of 56 µm. Particles as small as 0.2 µm and as large as 150 µm were detected. A sample of the micronised metallurgical grade silicon was etched for 15 minutes in a 1:1 by volume mixture of HF and ethanol. Following filtering, the powder was dried overnight in a Shel Lab evacuable oven at 32° C. Two 100 mg batches of as received (i.e. untreated) and the HF treated bulk silicon powders were added separately to 2 ml aliquots of fresh human saliva. Human pre-molars were then soaked in the two agitated solutions for 10 minutes. Following removal, the teeth were rinsed for 5 seconds. FIG. 4a shows a 1000× image of the porosified part of the enamel exposed to the as received, untreated powder solution. The associated EDX spectrum (5 keV beam, magnification 17000) in FIG. 4b illustrates that the particles are non-porous in nature, due to the weak oxygen signals. FIG. 4c shows a 330× image of a relatively smooth region of the tooth exposed to the HF treated powder. There are relatively few microparticles adhered but the higher magnification image in FIG. 4d reveals a substantially uniform coverage of submicron particles. The associated EDX spectrum showed weak silicon and oxygen signals.

Example 5

Controlled Release of Flavouring Agents

Figure 5:
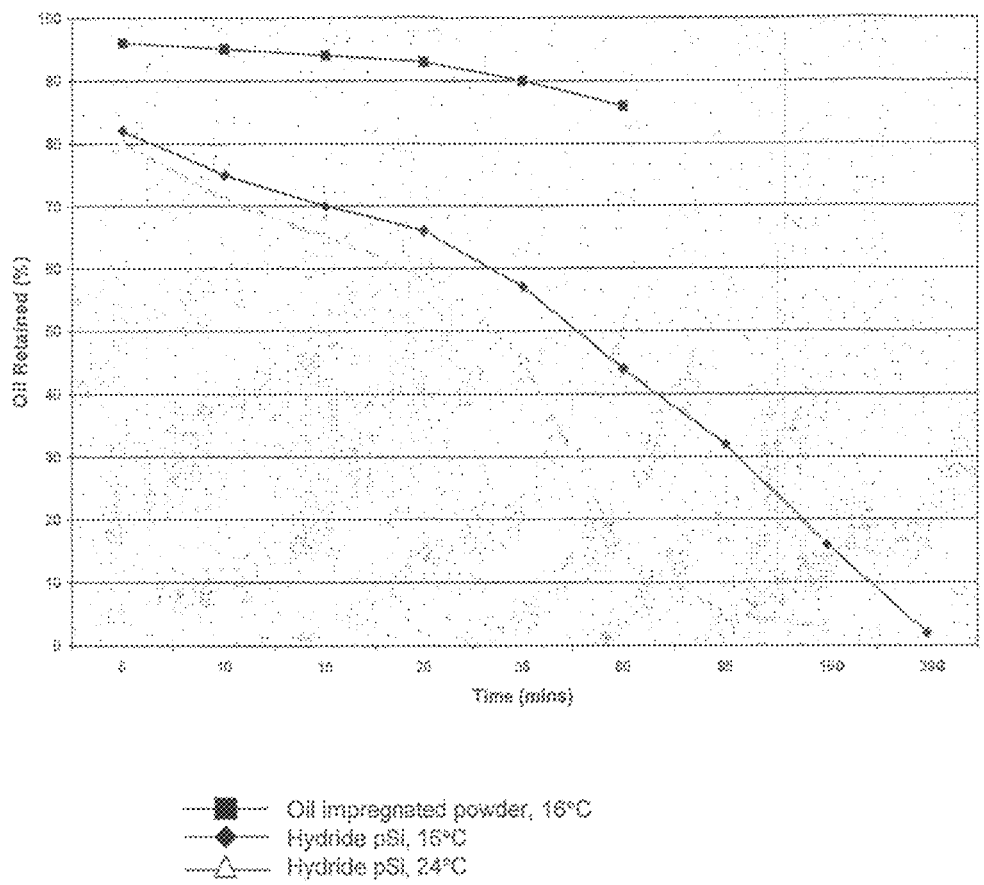
FIG. 5 is a plot of oil retained (%) in mesoporous silicon samples against time (mins) at 16° C. and 24° C.

A wafer segment of bulk silicon coated with a mesoporous layer (10.91 µm thickness) was loaded with peppermint oil and, using a gravimetric technique, its weight was monitored, at 16° C. and 24° C., as the volatile oil slowly evaporated from the pores. A suitable gravimetric technique is described in "Gravimetric analysis of pore nucleation and propagation in anodised silicon" by Brumhead et al, in Electrochimica Acta, vol. 38, pp191-197, (1993). A comparison was made with mesoporous particles derived from a silicon membrane of 140 thickness and 74% porosity. The results are shown in FIG. 5. In a further experiment, high porosity (82 vol %) of mesoporous silicon particles were mechanically sieved such that the diameters of the particles were between 75-100 µm. These particles were subjected to vigorous brushing against a polished silicon wafer using a commercially available toothbrush with hard grade nylon brushes. Following brushing, the majority of the particles possessed a diameter less than 50 µm with a substantial fraction below 15 µm in diameter.

The invention claimed is:

1. A dentifrice composition comprising a particulate elemental silicon abrasive agent wherein the silicon consists of elemental silicon.

2. A dentifrice composition according to claim 1, wherein the silicon is selected from one or more of: amorphous silicon; single crystal silicon; and
polycrystalline silicon.

3. A dentifrice composition according to claim 1, wherein the silicon is porous silicon.

4. A dentifrice composition according to claim 3, wherein the porous silicon has a BET surface area of 100 to 700 $m^2/g$.

5. A dentifrice composition according to claim 4, wherein the porous silicon has a BET surface area of 200 to 500 $m^2/g$.

6. A dentifrice composition according to claim 3, wherein the silicon is microporous or mesoporous.

7. A dentifrice composition according to claim 1, wherein the silicon is resorbable.

8. A dentifrice composition according to claim 1, wherein the silicon is about 96 to 99.9% pure.

9. A dentifrice composition according to claim 3, wherein the porous silicon consists surface modified porous silicon.

10. A dentifrice composition according to claim 9, wherein the surface modified porous silicon comprises, or consists essentially of, one or more of: derivatised porous silicon, partially oxidised porous silicon, porous silicon modified with silicon hydride surfaces.

11. A dentifrice composition according to claim 1, wherein the mean particle size ($d_{50}$) of the silicon abrasive agent is about 1 to 100 µm.

12. A dentifrice composition according to claim 11, wherein $d_{50}$ is about 10 to 50 µm.

13. A dentifrice composition according to claim 12, wherein $d_{50}$ about 30 µm.

14. A dentifrice composition according to claim 1, wherein the Vickers hardness of the particulate silicon abrasive agent is about 1 to 4 GPa.

15. A dentifrice composition according to claim 14, wherein the Vickers hardness is about 1 to 2 GPa.

16. A dentifrice composition according to claim 1, wherein the silicon abrasive agent is loaded with at least one active and/or inactive ingredients for delivery to the teeth and/or other oral surfaces.

17. A dentifrice composition according to claim 16, wherein the active and/or inactive ingredients are selected from any one or more of: an antitartar agent, flavouring agent, antiseptic, anticaries agent, antibacterial agent.

18. A dentifrice composition according to claim 1, wherein the particulate silicon abrasive agent is present in an amount of about 5 to 50 wt % of the dentifrice composition.

19. A dentifrice composition according to claim 1, wherein the silicon abrasive agent comprises bioactive silicon.

20. A dentifrice composition according to claim 19, wherein the bioactive silicon is loaded with calcium and/or phosphate salts.

21. A dentifrice composition according to claim 1, wherein the dentifrice composition is selected from a toothpaste, tooth powder, prophylaxis paste, lozenge, dragee, bon-bon, gum or oral gel.

22. A dentifrice composition according to claim 21, wherein the dentifrice composition is a toothpaste.

23. A dentifrice composition according to claim 1, wherein the silicon abrasive agent is at least partly present in the form of minors, each minor comprising a plurality of layers and wherein each layer comprises porous silicon.

24. A dentifrice composition according to claim 1, wherein the pH of the dentifrice composition is less than or equal to about 7.

25. A dentifrice composition according to claim 1, wherein the RDA of the dentifrice composition is about 10 to 150.

26. A dentifrice composition according to claim 25, wherein the RDA is less than about 100.

27. A dentifrice composition according to claim 1 wherein the PCR is about 20 to 150.

28. A dentifrice composition according to claim 27, wherein the PCR is greater than about 50.

29. A production process for making the dentifrice composition according to claim 1, comprising blending the particulate silicon abrasive agent and other components of the dentifrice composition.

30. A production process according to claim 29, wherein the other components are selected from one or more of the following: water, humectant, anticaries agent, antitartar agent, antibacterial agent, other abrasive agent, flavouring agent, thickening agent, surfactant, efficacy enhancing agent, preservative, silicone, desensitiser, whitening agent, acidity regulator, pigment.

31. A method for reducing stain and/or plaque and/or gingivitis comprising the application of a safe and effective amount of a dentifrice composition according to claim 1 to the teeth and other oral surfaces.

32. A cosmetic method for reducing stain comprising the application of a safe and effective amount of a composition according to claim 1 to the teeth and other oral surfaces.

33. A dentifrice composition according to claim 1 for use in the treatment and/or the prevention of plaque and/or gingivitis.

* * * * *